United States Patent
Lee et al.

(10) Patent No.: US 7,268,228 B2
(45) Date of Patent: Sep. 11, 2007

(54) OPTICALLY ACTIVE AZIRIDINE-2-CARBOXYLATE DERIVATIVES AND A PROCESS FOR PREPARING THEM

(75) Inventors: Won Koo Lee, Seoul (KR); Chan Sun Park, Seoul (KR); Yeon Hwa Lim, Seoul (KR); Hyun J on Ha, Seoul (KR)

(73) Assignee: Imagene Co., Ltd. (KR)

( * ) Notice: Subject to any disclaimer, the term of this patent is extended or adjusted under 35 U.S.C. 154(b) by 530 days.

(21) Appl. No.: 10/344,225

(22) PCT Filed: Aug. 10, 2001

(86) PCT No.: PCT/KR01/01360

§ 371 (c)(1),
(2), (4) Date: Jul. 30, 2003

(87) PCT Pub. No.: WO02/12186

PCT Pub. Date: Feb. 14, 2002

(65) Prior Publication Data

US 2004/0030133 A1    Feb. 12, 2004

(30) Foreign Application Priority Data

Aug. 10, 2000  (KR) .............................. 2000/46387

(51) Int. Cl.
C07D 251/16    (2006.01)
C07D 203/16    (2006.01)
C07D 203/04    (2006.01)

(52) U.S. Cl. ..................... 544/215; 548/966; 548/968; 548/969

(58) Field of Classification Search ................ 544/215; 548/966, 968, 969
See application file for complete search history.

(56) References Cited

OTHER PUBLICATIONS

G.V. Shustov et al., Asymmetric Synthesis And Lactonization of 1-beta-Hydroxyalkylaziridine-2-Carboxylic Esters Into 4-Oxa-1Azabibyblo[4.1.0] Heptane-5-ones, Tetrahedron vol. 46, No. 19, pp. 6741-6752, 1990.*

* cited by examiner

Primary Examiner—Johann Richter
Assistant Examiner—Ebenezer Sackey
(74) Attorney, Agent, or Firm—Baker & McKenzie LLP

(57) ABSTRACT

This invention relates to compounds of Formula I having an aziridine-2-carboxylic group and a menthol group, a process for preparing such compounds, a method for obtaining optically active aziridine-2-carboxylate derivatives by optical resolution of such compounds, and optically active aziridine-2-carboxylate derivatives obtained by the same method:

(I)

wherein $R^1$ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl and 4-methoxyphenyl; 2,4-dimethoxyphenyl; substituted phenyl including (1R)-phenylethyl or (1S)-phenylethyl. Preferences are given to (1R)-phenylethyl and (1S)-phenylethyl. Menthol is selected from the group consisting of (+)-menthol and (−)-menthol.

20 Claims, No Drawings

OPTICALLY ACTIVE AZIRIDINE-2-CARBOXYLATE DERIVATIVES AND A PROCESS FOR PREPARING THEM

CROSS-REFERENCE TO RELATED APPLICATIONS

This application is a § 371 application of PCT Application No. PCT/KR01/01360 filed on Aug. 10, 2001, which claims priority to Korean Application No. 2000/46387 filed on Aug. 10, 2000.

TECHNICAL FIELD

Optically active aziridine is not only of value in itself, but also a useful compound for making a variety of fine chemicals including medicaments via simple transformation.

BACKGROUND ART

Thus, preparations for aziridine have been studied for a long time, and there are several methods of the preparations. The synthesis of aziridine may be carried out as well known in the art, for example, by the synthesis from optically active serine as an amino acid (cf. J. E. Baldwin et al., *Tetrahedron Lett.*, 1996, 37, 3761–3764), by the reaction of imine via asymmetric aziridination (cf. J. C. Antilla et al., *J. Am. Chem. Soc.*, 1999, 121, 5099–5100), by the asymmetric aziridination of alkene (cf. K. B. Hansen et al., *Angew. Chem. Int. Ed. Engl.* 1955, 34, 676–679) etc. The preparation of aziridine from serine can only produce aziridine of natural steric configuration of serine. Even by the other asymmetric methods, it is difficult to produce aziridine on a large scale in one step. It is also impossible to attain more than 99% of optical purity. Other methods can obtain optically active aziridine from the chiral sulfine (F. A. Davis, U.S. Pat. No. 5,789,599) or from optical resolution via enzyme (F. Kaoru, Japanese Patent No. 4,046,153). However, those methods are not practical because it is difficult to produce each starting material.

DISCLOSURE OF THE INVENTION

The present invention relates to a compound of Formula I having an aziridine-2-carboxylic group and a menthol group:

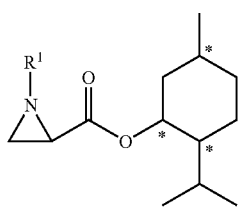

(I)

wherein $R^1$ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl and 4-methoxyphenyl; 2,4-dimethoxyphenyl; substituted phenyl including (1R)-phenylethyl or (1S)-phenylethyl. Given preferences are (1R)-phenylethyl and (1S)-phenylethyl. Menthol is chosen from the group consisting of (+)-menthol and (−)-menthol.

In one preferred embodiment, the present invention provides a process for producing the compound of Formula I having an aziridine-2-carboxylic group and a menthol group by reacting 2,3-dibromopropanoate menthol ester with amine $R^1NH_2$.

In another preferred embodiment, the present invention provides a process for producing aziridine-2-carboxylate derivatives compounds of Formula II or hydroxymethylaziridine compounds of Formula III by transesterifying or reducing the compound I.

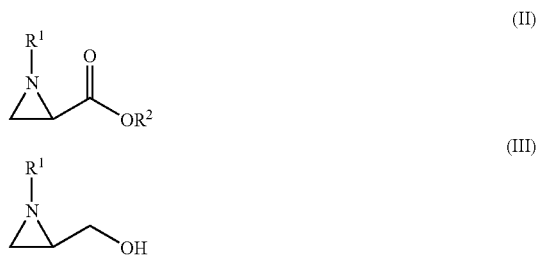

wherein $R^1$ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl and 4-methoxyphenyl; 2,4-dimethoxyphenyl; substituted phenyl including (1R)-phenylethyl or (1S)-phenylethyl. Preferences are given to (1R)-phenylethyl, (1S)-phenylethyl.

$R^2$ is hydrogen, substituted or unsubstituted $C_1$~$C_{40}$ hydrocarbon radical, wherein the substituent(s) on $C_1$~$C_{40}$ hydrocarbon radical is/are 0 to 40 halogen atoms; or heteroatom selected from the group consisting of boron, nitrogen, oxygen, sulfur, phosphorous, silicon and selenium. More preferably, $R^2$ is $C_1$~$C_{10}$ alkyl group. Most preferably, $R^2$ is methyl or ethyl group, In still another preferred embodiment, the present invention provides a process for obtaining optically active aziridine-2-carboxylate menthol ester derivatives by optical resolution of the compound I.

In still another preferred embodiment, the present invention provides an optically active compound obtained by the optical resolution.

According to the present invention, it is possible to obtain optically active aziridines in high yields of more than 95% by reacting 2,3-dibromopropanoate (−)-menthol ester or (+)-menthol ester with amine, which is more convenient than conventional processes for producing optically active aziridines. The alkyl ester of aziridine can be obtained by making the obtained diastereomer in an optically pure form, and transesterifying the menthol esters with alcohols under base. All esters may be reduced with a known reducing agent such as lithium aluminum hydride or sodium borohydride to produce (2R)- and (2S)-hydroxymethylaziridine. The obtained aziridine can be transformed into other fine chemicals including medicaments and their intermediates.

One embodiment of the present invention provides a compound of Formula I comprising an aziridine-2-carboxylic group and a menthol group.

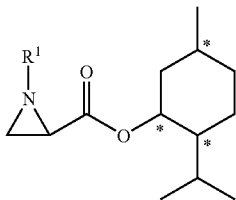

(I)

wherein $R^1$ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl, and 4-methoxyphenyl; 2,4-dimethoxyphenyl; substituted phenyl including (1R)-phenylethyl or (1S)-phenylethyl. Preferences are given to (1R)-phenylethyl, (1S)-phenylethyl. Menthol is selected from the group consisting of (+)-menthol and (−)-menthol.

Another embodiment of the present invention provides a process for producing a compound of Formula I comprising an aziridine-2-carboxylic group and a menthol group.

The compound of Formula I is synthesized by reacting 2,3-dibromopropanoate (−)-menthol ester or (+)-menthol ester with amine of formula $R^1NH_2$ wherein $R^1$ is as defined above. The reactant amine should be nucleophilic primary amine regardless of whether it is chiral or not. According to the type of the reactant amine, corresponding (2R)- and (2S)-aziridine-2-carboxylate (−)-menthol ester or (+)-menthol ester can be obtained.

By reacting 2,3-dibromopropanoate (−)-menthol ester with (1R)-phenylethylamine, diastereomer mixtures of (2R)- and (2S)-N-[(1R)-phenylethyl]aziridine-2-carboxylate (−)-menthol ester having formula I can be obtained. Also, the reaction of the (−)-menthol ester with (1S)-phenylethylamine produces the diastereomer mixtures of (2R)- and (2S)-N-[(1S)-phenylethyl]aziridine-2-carboxylate (−)-menthol ester.

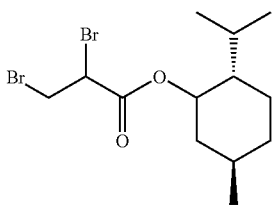

2,3-dibromopropanoate (−)-menthol ester

By reacting 2,3-dibromopropanoate (+)-menthol ester with (1R)-phenylethylamine, diastereomer mixtures of (2R)- and (2S)-N-[(1R)-phenylethyl]aziridine-2-carboxylate (+)-menthol ester having formula I can be obtained. Also, the reaction of the (+)-menthol ester with (1S)-phenylethylamine produces the diastereomer mixtures of (2R)- and (2S)-N-[(1S)-phenylethyl]aziridine-2-carboxylate (+)-menthol ester.

Preferably, the reaction can be carried out in the presence of base, such as amines or inorganic bases. As such amines, for example, tertiary amines which can generally function as base are preferred. Preferences are given to pyridines and trialkylamines such as diisopropylethylamine, tributylamine, triethylamine, etc. Such inorganic bases, for example, include alkali metal base such as potassium carbonate, sodium carbonate, sodium hydrogen carbonate and potassium hydrogen carbonate, preferably potassium carbonate.

The reaction may be carried out in n-hexane when amines including triethylamine etc. are used as base, and in acetonitrile when potassium carbonate is used as base.

The present invention relates to a process for producing aziridine-2-carboxylate derivatives of Formula II or hydroxymethylaziridine compounds of Formula III, comprising transesterifying or reducing the compound of Formula I.

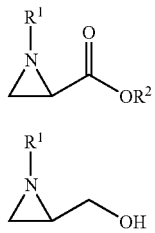

(II)

(III)

wherein $R^1$ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl, and 4-methoxyphenyl; 2,4-dimethoxyphenyl; substituted phenyl including (1R)-phenylethyl or (1S)-phenylethyl. Preferences are given to (1R)-phenylethyl or (1S)-phenylethyl.

$R^2$ in alcohol ($R^2OH$) which is used as a reactant in transesterification, is hydrogen, substituted or unsubstituted $C_1$~$C_{40}$ hydrocarbon radical, wherein the substituent(s) of $C_1$~$C_{40}$ hydrocarbon radical is/are 0 to 40 halogen atoms; and heteroatom selected from the group consisting of boron, nitrogen, oxygen, sulfur, phosphorus, silicon and selenium. More preferably, $R^2$ is $C_1$~$C_{10}$ alkyl group. Most preferably, $R^2$ is methyl or ethyl group.

In the reduction of the compound of Formula I, conventional ester reducing agents may be used as reducing agents. Those skilled in the art may easily select suitable ester reducing agents. Typical ester reducing agents include lithium aluminum hydride, sodium borohydride, lithium borohydride and calcium borohydride. Bouveault-Blanc reaction, which is carried out the reduction using sodium in ethanol, may be used.

Optically active aziridine-2-carboxylate menthol ester derivatives can be obtained from the optical resolution of the aziridine compounds of Formula I.

Resolution methods useful in the present invention are fractional crystallization, chromatography, recrystallization, etc.

Fractional crystallization is an operation which separates each component from a mixture by partially precipitating a component in a crystalline form and dissolving it, utilizing the difference of solubilities. Substantially pure products can be obtained by repeating such an operation.

Stereoisomers can be resolved by column chromatography, utilizing mixtures of hexane/ethyl acetate (4/1).

Also recrystallization may be used as a resolution method, which has an advantage of resolving large quantities of isomers at one time. Solvents useful in the recrystallization are disclosed in U.S. Pat. No. 5,789,599. Alcohol, hydrocarbon, ketone, carboxylic acid, ether, benzene and substituted benzene are generally used as solvents. Particularly, $C_1$~$C_5$ alcohol or $C_5$~$C_{12}$ hydrocarbon, more preferably ethanol or n-hexane is used as solvent.

By the recrystallization in ethanol of the isomer mixtures of amine comprising (1R)-phenylethyl or (1S)-phenylethyl as $R^1$, (2R)-N-[(1R)-phenylethyl]aziridine-2-carboxylate (−)-menthol ester or (2S)-N-[(1S)-phenylethyl]aziridine-2-carboxylate (−)-menthol ester is obtained as crystals. Recrystallization in n-hexane produces (2R)-N-[(1S)-phenylethyl]aziridine-2-carboxylate (−)-menthol ester or (2S)-N-[(1R)-phenylethyl]aziridine-2-carboxylate (−)-menthol ester as crystals. The other part of the diastereomer remains in the solution in a dissolved form.

The optically active aziridine-2-carboxylate derivatives can be obtained from resolution and purification of the diastereomer by the optical resolution method as described above.

The derivatives include the following compounds.

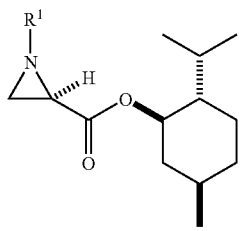

(2R)-[N—$R^1$]aziridine-2-carboxylate (−)-menthol ester

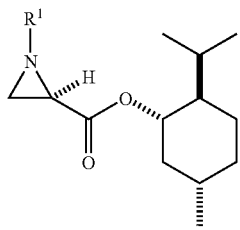

(2R)-[N—$R^1$]aziridine-2-carboxylate (+)-menthol ester

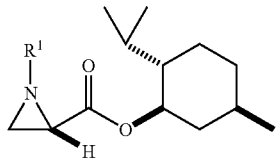

(2S)-[N—$R^1$]aziridine-2-carboxylate (−)-menthol ester

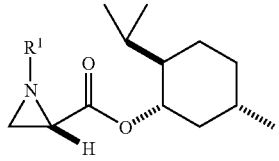

(2S)-[N—$R^1$]aziridine-2-carboxylate (+)-menthol ester

When amines having (1R)-phenylethyl and (1S)-phenylethyl as $R^1$ are used, the following optically active isomer compounds can be obtained.

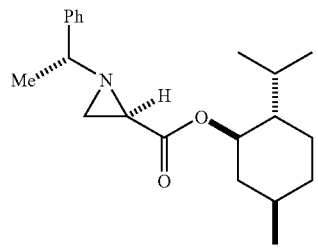

(2R)-[N-(1R)-phenylethyl]aziridine-2-carboxylate (−)-menthol ester
mp: 73–75° C., $[\alpha]_D^{24}$=+14.9 (c=5, in $CHCl_3$)

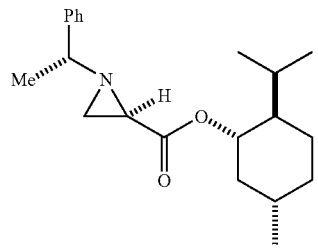

(2R)-[N-(1R)-phenylethyl]aziridine-2-carboxylate (+)-menthol ester
mp: 80–81° C., $[\alpha]_D^{24}$=+137.1 (c=5, in $CHCl_3$)

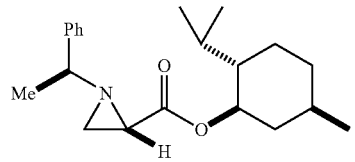

(2S)-[N-(1S)-phenylethyl]aziridine-2-carboxylate (−)-menthol ester
mp: 77–78° C., $[\alpha]_D^{24}$=−136.8 (c=5, in $CHCl_3$)

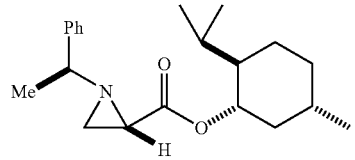

(2S)-[N-(1S)-phenylethyl]aziridine-2-carboxylate (+)-menthol ester
mp: 72–73° C., $[\alpha]_D^{24}$=−14.8 (c=5, in $CHCl_3$)

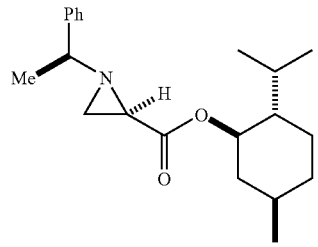

(2R)-[N-(1S)-phenylethyl]aziridine-2-carboxylate (−)-menthol ester
mp: 59–61° C., $[\alpha]_D^{24}$=−58.3 (c=5, in $CHCl_3$)

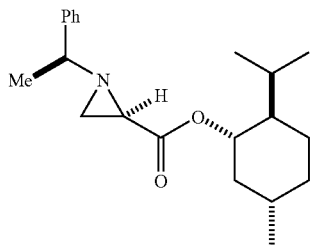

(2R)-[N-(1S)-phenylethyl]aziridine-2-carboxylate (+)-menthol ester mp: 64–65° C., $[\alpha]_D^{24}=+61.5$ (c=5, in $CHCl_3$)

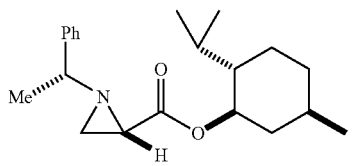

(2S)-[-(1R)-phenylethyl]aziridine-2-carboxylate (−)-menthol ester mp: 65–67° C., $[\alpha]D^{24}=-61.0$ (c=5, in $CHCl_3$)

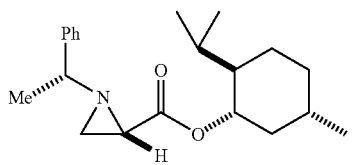

(2S)-[N-(1R)-phenylethyl]aziridine-2-carboxylate (+)-menthol ester mp: 60–63° C., $[\alpha]D^{24}=+58.7$ (c=5, in $CHCl_3$)

By transesterification of the obtained optically pure aziridine menthol ester with suitable alcohols, it is possible to produce alkyl esters of aziridine-2-carboxylate which has the stereochemistry equivalent to that of the menthol ester, at 2-position carbon atom in an optically active aziridine ring. The alcohol used in this process can be the same as used in transesterification of the mixture of the diastereomer. Also, the same reducing agents can be used for reduction.

The obtained products include (2R)-[N—$R^1$]aziridine-2-carboxylate alkyl ester and (2S)-[N—$R^1$]aziridine-2-carboxylate alkyl ester.

Preferences are given to optically active (2R)-[N—$R^1$]aziridine-2-carboxylate and (2S)-[N—$R^1$]aziridine-2-carboxylate methyl or ethyl ester.

When amine in which $R^1$ is (1R)-phenylethyl or (1S)-phenylethyl is used as amine and methanol is used as alcohol, (2R)-[N-(1R)-phenylethyl]aziridine-2-carboxylate methyl ester, (2S)-[N-(1R)-phenylethyl]aziridine-2-carboxylate methyl ester, (2R)-[N-(S)-phenylethyl]aziridine-2-carboxylate methyl ester or (2S)-[N-(1S)-phenylethyl]aziridine-2-carboxylate methyl ester is produced. When using the same amine and ethanol as alcohol, (2R)-[N-(1R)-phenylethyl]aziridine-2-carboxylate ethyl ester, (2S)-[N-(1R)-phenylethyl]aziridine-2-carboxylate ethyl ester, (2R)-[N-(1S)-phenylethyl]aziridine-2-carboxylate ethyl ester or (2S)-[N-(1S)-phenylethyl]aziridine-2-carboxylate ethyl ester is produced.

EXAMPLES

The following examples are given for the purpose of illustrating the present invention and shall not be construed as being limitations on the scope or spirit of the invention.

Example 1

Synthesis of 2,3-dibromopropanoate (−)-menthol Ester 17 g of (−)-menthol was dissolved in methylene chloride, and 16.7 g of triethylamine was then added. The mixture solution was cooled to 0° C. A solution dissolving 10.0 g of acryloyl chloride in methylene chloride (220 ml) was slowly added into the mixture solution at 0° C. After completing the addition, the reaction temperature was allowed to raise to ambient temperature. The reaction was continued for 18 more hours. After finishing the reaction, the solvent was removed, 300 ml of water was added to the residue, and the product was extracted three times with 300 ml of petroleum ether. After extraction, the organic extracts of petroleum ether were dried under anhydrous $MgSO_4$, filtered and concentrated in vacuo. 6.90 g of a sample, taken from the resulting product, was dissolved in 140 ml methylene chloride. 7.94 g of bromine dissolved in 20.0 ml of methylene chloride was slowly added dropwise to the solution with stirring. The solution was reacted at ambient temperature for about 18 hours. After adding an aqueous saturated solution of $Na_2S_2O_3$ to remove bromine, the solution was extracted three times with 200 ml of petroleum ether. The organic extracts were dried under anhydrous magnesium sulfate, filtered, concentrated in vacuo to give the product, which is then purified by the vacuum distillation.

$^1H$ NMR (200 MHz, $CDCl_3$) δ 4.75 (m, 1H), 4.13 (m, 1H), 3.90 (tt, J=11.4 Hz, 1.6 Hz, 1H), 3.64 (dd, J=10, 4.4 Hz, 1H), 1.99 (m, 2H), 1.72–1.65 (m, 2H), 1.50–1.42 (m, 3H), 1.11–0.74 (m, 12H).

Example 2

Synthesis of (2R)-[N-(1R)-phenylethyl]aziridine-2-carboxylate (−)-menthol ester and (2S)-[N-(1R)-phenylethyl]aziridine-2-carboxylate (−)-menthol ester 212 mg of 2,3-dibromopropanoate (−)-menthol ester was dissolved in 5.0 ml of acetonitrile and 239 ng of potassium carbonate was then added. After adding (2R)-phenylethylamine, the solution was stirred at ambient temperature for 12 hours. After completing the reaction, 10.0 ml of water was added to the product. The product was extracted twice with 30.0 ml of petroleum ether. The organic extracts were dried under the anhydrous magnesium sulfate, filtered and concentrated in vacuo to give the titled product.

Mixture of diastereomers of (2R)-[N-(1R)-phenylethyl]aziridine-2-carboxylate (−)-menthol ester and (2S)-[N-(1R)-phenylethyl]aziridine-2-carboxylate (−)-menthol ester $^1H$ NMR (200 MHz, $CDCl_3$) δ 7.36–7.22 (m, 5H), 4.70 (td, J=10.7, 4.4 Hz, 1H), 2.57 (q, J=6.3 Hz, 1H), 2.35–1.86 (m, 4H), 1.80–0.47 (m, 20H).

The resulting solid product (8.7 g) was dissolved in 70 ml of alcohol, then recrystallized at −10 C and filtered to give (2R)-[N-(1R)-phenylethyl]aziridine-2-carboxylate (−)-menthol ester (2.2 g). The resulting solution was concentrated again, dissolved in 50 ml of alcohol and then recrystallized to obtain (2R)-[N-(1R)-phenylethyl]aziridine-2-carboxylate (−)-menthol ester (1.2 g). Methanol, ethanol or other alcohols can be used as alcohol. Crystal was obtained through recrystallization, and the remaining solution was thoroughly distilled under reduced pressure. 50 ml of hydrocarbon solution was added to the resulting partially solid material (5.3 g). The solution was then recrystallized at −15° C. to give (2S)-[N-(1R)-phenylethyl]aziridine-2-carboxylate (−)-menthol ester (1.9 g). The remaining solution was concentrated, dissolved in 30 ml of hydrocarbon solvent and then recrystallized to produce (2S)-[N-(1R)-phenylethyl]aziridine-2-carboxylate (−)-menthol ester (0.8 g). As hydrocarbon solvents, pentane, hexane, heptane, cyclohexane etc. may be used. The remaining solution from recrystallization was combined with the initial mixture of isomer solution to repeat the procedure of the example. Instead of recrystallization, the column chromatography using hexane/ethyl acetate (4/1) mixture solvent can be used for separation.

(2S)-[N-(1R)-phenylethyl]aziridine-2-carboxylate (−)-menthol Ester $^1$H NMR (500 MHz, CDCl$_3$) δ 7.36–7.22 (m, 5H), 4.70 (td, J=10.7, 4.4 Hz, 1H), 2.57 (q, J=6.3 Hz, 1H), 2.32 (dd, J=2.9, 1.0 Hz, 1H), 2.01 (dd, J=6.3, 2.9 Hz, 1H), 1.91(m, 1H), 1.85(m, 1H), 1.76 (dd, J=10.0, 1.0 Hz, 1H), 1.67–1.62 (m, 2H), 1.45 (d, J=6.3 Hz, 3H), 1.41–1.37(tt, J=6.3, 3.4 Hz 1H), 1.06–0.97(m, 2H), 0.94–0.89(m, 1H), 0.89(d, J=6.8 Hz, 3H), 0.88(d, J=6.8 Hz, 3H), 0.87–0.79(m, 1H), 0.71(d, J=6.8 Hz, 3H).

(2R)-[N-(1R)-phenylethyl]aziridine-2-carboxylate (−)-menthol ester $^1$H NMR (200 MHz, CDCl$_3$) δ 7.36–7.22 (m, 5H), 4.70 (td, J=10.7, 4.4 Hz, 1H), 2.57 (q, J=6.3 Hz, 1H), 2.18–1.89 (m, 4H), 1.73–1.45 (m, 8H), 1.26–0.74(m, 14H).

Example 3

Synthesis of (2R)-[N-(1R)-phenylethyl]aziridine-2-carboxylate (−)-menthol ester and (2S)-[N-(1R)-phenylethyl]aziridine-2-carboxylate (−)-menthol ester 10.0 g of 2,3-dibromopropanoate (−)-menthol ester was dissolved in 130 ml of hexane, and 8.25 g of triethylamine was then added. After slowly adding a solution of of (R)-1-phenylethylamine (3.29 g) dissolved in hexane (100 ml), the solution was stirred at ambient temperature for 12 hours. After completing the reaction, 200 ml of water was added to the reactants, and the product was extracted twice with 200 ml of petroleum ether. The organic extracts were dried under anhydrous magnesium sulfate, filtered and concentrated in vacuo to give the titled product.

The product was resoluted by column chromatography eluting with hexane/ethyl acetate (4/1) mixture solvent to give two forms of the separated stereomers.

Example 4

Synthesis of (2R)-[N-(1S)-phenylethyl]aziridine-2-carboxylate (−)-menthol ester and (2S)-[N-(1S)-phenylethyl]aziridine-2-carboxylate (−)-menthol ester Using the analogous procedure described in Example 2 or 3, and replacing (1R)-phenylethylamine with (1S)-phenylethylamine, the titled compounds were produced.

(2R)-[N-(1S)-phenylethyl]aziridine-2-carboxylate (−)-menthol ester $^1$H NMR (500 MHz, CDCl$_3$) δ 7.34–7.25 (m, 5H), 4.74 (td, J=10.1, 4.4 Hz, 1H), 2.57 (q, J=6.6 Hz, 1H), 2.23–2.14 (m, 1H), 2.06–1.35 (m, 9H), 1.12–0.69(m, 14H).

(2S)-[N-(1S)-phenylethyl]aziridine-2-carboxylate (−)-menthol ester $^1$H NMR (200 MHz, CDCl$_3$) δ 7.24–7.45 (m, 5H), 4.79 (td, J=10.5, 4.4 Hz, 1H), 2.58 (q, J=6.2 Hz, 1H), 2.213–1.91 (m, 4H), 1.74–1.42 (m, 8H), 1.18–0.81(m, 12H).

Example 5

Synthesis of (2R)-[N-(1S)-phenylethyl]aziridine-2-carboxylate ethyl ester

After dissolving (2R)-[N-(1S)-phenylethyl]aziridine-2-carboxylate (−)-menthol ester (167 mg) in 1.69 ml of ethanol, and then adding 280 mg of potassium carbonate, the resulting solution was stirred at ambient temperature for two days. After completing the stirring, the solids were filtered. The residual solution was concentrated in vacuo and distilled in vacuo to recover the (−)-menthol and to give the titled (2R)-N-[(1S)-phenylethyl]aziridine-2-carboxylate ethyl ester.

$^1$H NMR (200 MHz, CDCl$_3$) δ 7.25 (m, 5H), 4.13 (q, J=7.2 Hz, 2H), 2.56 (q, J=6.6 Hz, 1H), 2.32 (dd, J=6.4, 3.2 Hz, 1H), 2.05 (d, J=2.2 Hz, 1H), 1.76 (dd, J=6.3, 1.0 Hz, 1H), 1.45 (d, J=6.6 Hz, 3H), 1.21 (t, J=7.2 Hz, 3H).

Example 6

Synthesis of (2S)-[N-(1S)-phenylethyl]aziridine-2-carboxylate Ethyl Ester

Using the analogous procedure described in Example 5 and (2S)-N-[(1S)-phenylethyl]aziridine-2-carboxylate (−)-menthol ester as starting material, (2S)-[N-(1S)-phenylethyl]aziridine-2-carboxylate ethyl ester was produced.

$^1$H NMR (300 MHz, CDCl$_3$) δ 7.33 (m, 5H), 4.23 (m, 2H), 2.54 (q, J=6.6 Hz, 1H), 2.20 (dd, J=6.4, 3.2 Hz, 1H), 2.10 (d, J=2.2 Hz, 1H), 1.59 (dd, J=6.3, 1.0 Hz, 1H), 1.48 (d, J=6.6 Hz, 3H), 1.31 (t, J=7.2 Hz, 3H).

Example 7

Synthesis of (2R)-[N-(1S)-phenylethyl]aziridine-2-carboxylate methyl ester

Using the analogous procedure described in Example 5 and replacing ethyl alcohol with methyl alcohol, the titled compound was produced.

$^1$H NMR (200 MHz, CDCl$_3$) δ 7.27–7.35(5H, m), 3.68 (3H, s), 2.57 (1H, q, J=6.7) 2.34 (1H, dd, J=3.2, 0.8 Hz), 2.09 (1H, dd, J=6.8, 3.0 Hz), 1.79 (1H, dd, J=6.8, 3.0 Hz), 1.47 (3H, d, J=6.6 Hz).

Example 8

Synthesis of (2S)-[N-(1S)-phenylethyl]aziridine-2-carboxylate Methyl Ester

Using the analogous procedure described in Example 5 and replacing ethyl alcohol with methyl alcohol, the titled compound was produced.

¹H NMR (200 MHz, CDCl₃) δ 7.25–7.41 (5H, m), 3.75 (3H, s), 2.54 (1H, q, J=6.7) 2.22 (1H, dd, J=6.2, 3.1 Hz), 2.14 (1H, dd, J=3.1, 1.4 Hz), 1.62 (1H, dd, J=6.2, 1.4 Hz), 1.48 (3H, d, J=6.6 Hz).

Example 9

Synthesis of (2R)-N-[(1S)-phenylethyl]-2-hydroxymethyl aziridine 100 mg of (2R)-[N-(S)-1-phenylethyl]aziridine-2-carboxylate ester obtained from Example 2, 3, 4, 5, 6 or 7 was dissolved in 3.0 ml of diethylether, 23 mg of LiAlH₄ was then added at 0° C. in portionwise. After completing the addition, the solution was stirred at ambient temperature for 15 more minutes, 10.0 ml of water was added, and the product was extracted twice with 10.0 ml of diethyl ether. The organic extracts were dried under anhydrous magnesium sulfate, filtered and concentrated in vacuo to give the titled product.
¹H NMR (200 MHz, CDCl₃) δ 7.36–7.26 (m, 5H), 3.61 (dd, J=11.5, 3.6 Hz, 1H), 3.33 (dd, J=11.5, 5.2 Hz, 1H), 2.54 (q, J=6.6 Hz, 1H), 1.93 (d, J=3.5 Hz, 1H), 1.74–1.66 (m, 1H), 1.50(d, J=6.5, 1H), 1.43 (d, J=6.6 Hz, 3H).

Example 10

Synthesis of (2S)-N-[(1S)-phenylethyl]-2-hydroxymethyl Aziridine

Using the analogous procedure described in Example 9 and (2S)-N-[(1S)-phenylethyl]aziridine-2-carboxylate ester obtained from Example 4 or 6 as starting material, the titled product was quantitatively obtained.
¹H NMR (200 MHz, CDCl₃) δ 7.36–7.26 (m, 5H), 3.88 (dd, J=11.5, 3.6 Hz, 2H), 3.53–3.43 (m, 1H), 2.54 (q, J=6.6 Hz, 1H), 1.85 (m, 1H), 1.71(d, J=3.6 Hz, 1H), 1.49 (d, J=6.6 Hz, 3H).

According to this invention, large amounts of optically pure (2R)- and (2S)-aziridine-2-carboxylate ester, and (2R)- and (2S)-2-hydroxymethyl aziridine can be easily produced.

The present process can produce optically active aziridine in higher yield, i.e., at least 95%, by reacting 2,3-dibromopropanoate (−)-menthol ester with optically pure amine than any other known processes. The diastereomers obtained are optically resolved to give each stereomer in a completely optically pure form. By using the known reduction processes, useful compounds, such as (2R)-hydroxymethylaziridine or (2S)-hydroxymethylaziridine can be made. The obtained aziridine can be transformed into fine chemicals including medicine and their intermediates.

The invention claimed is:

1. A compound of Formula I having aziridine-2-carboxylic group and menthol group:

(I)

wherein R¹ is hydrogen; 4-chlorophenyl; 4-methoxyphenyl; s-triazinyl or pyridinyl acyl; benzyl; 2,4-dimethoxyphenyl; (1R)-phenylethyl or (1S)-phenylethyl, and menthol is selected from the group consisting of (+)-menthol and (−)-menthol.

2. The compound according to claim 1, wherein R¹ is (1R)-phenylethyl or (1S)-phenylethyl.

3. A process for producing a compounds of Formula I having aziridine-2-carboxylic group and menthol group, comprising the reaction of 2,3-dibromopropanoate menthol ester with amine R¹NH₂:

2,3-dibromopropanoate menthol ester (I)

wherein R¹ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl and 4-methoxyphenyl; 2,4-dimethoxyphenyl; substituted phenyl including (1R)-phenylethyl and (1S)-phenylethyl, and menthol is selected from the group consisting of (+)-menthol and (−)-menthol.

4. The process according to claim 3, wherein the amine is (R)-phenylethylamine or (S)-phenylethylamine.

5. The process according to claim 3, wherein the reaction is carried out under tertiary amine which can function as base, or under inorganic base.

6. The process according to claim 5, wherein the tertiary amine is amine selected from the group consisting of pyridine and trialkylamine including diisopropylethylamine, tributylamine or triethylamine, and the inorganic base is alkali metal carbonate selected from the group consisting of potassium carbonate, sodium carbonate, sodium hydrogen carbonate and potassium hydrogen carbonate.

7. The process according to claim 5, wherein the amine is triethylamine and the inorganic base is potassium carbonate.

8. A process for producing aziridine-2-carboxylate derivative of formula II or hydroxymethylaziridine of formula III, which comprises the transesterification or reduction of the compound as defined in claim 1.

(II)

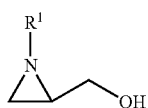

wherein R¹ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl, and 4-methoxyphenyl; 2,4-dimethoxyphenyl; substituted phenyl including (1R)-phenylethyl and (1S)-phenylethyl, R² is hydrogen, substituted or unsubstituted $C_1$~$C_{40}$ hydrocarbon radical, wherein the substituent(s) on $C_1$~$C_{40}$ hydrocarbon radical is/are 0 to 40 halogen atoms; or heteroatom selected from the group consisting of boron, nitrogen, oxygen, sulfur, phosphorous, silicon and selenium, more preferably, $C_1$~$C_{10}$ alkyl group, most preferably, methyl or ethyl group.

9. A process for obtaining optically active aziridine-2-carboxylate menthol ester derivatives as follows, which comprises optically resolving the compound of formula I having aziridine-2-carboxylic group and menthol group:

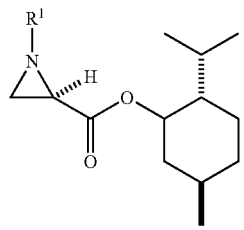

(2R)-[N—R¹]aziridine-2-carboxylate (−)-menthol ester

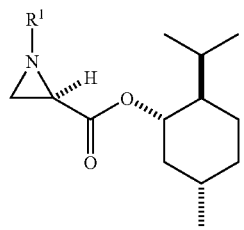

(2R)-[N—R¹]aziridine-2-carboxylate (+)-menthol ester

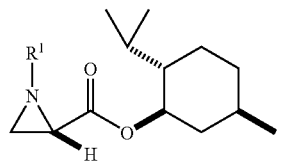

(2S)-[N—R¹]aziridine-2-carboxylate (−)-menthol ester

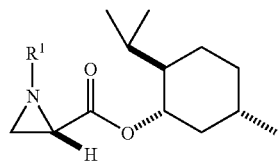

(2S)-[N—R¹]aziridine-2-carboxylate (+)-menthol ester

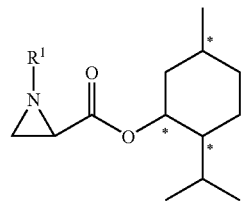

wherein R¹ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl, and 4-methoxyphenyl; 2,4-dimethoxyphenyl; substituted phenyl including (1R)-phenylethyl and (1S)-phenylethyl, and menthol is selected from the group consisting of (+)-menthol and (−)-menthol.

10. The process according to claim 9, wherein the optical resolution is carried out by one process selected from fractional crystallization, chromatography and recrystallization.

11. The process according to claim 10, wherein the optical resolution is carried out by recrystallization.

12. The process according to claim 11, wherein solvents for recrystallization include alcohol, hydrocarbon, ketone, carboxylic acid, ether, benzene or substituted benzene.

13. The process according to claim 11, wherein solvents for recrystallization are $C_1$~$C_5$ alcohol or $C_5$~$C_{12}$ hydrocarbon solvent are used.

14. The process according to claim 12, wherein the alcohol is ethanol and the hydrocarbon solvent is n-hexane.

15. An optically active compound having formula I resolved by the process claimed in claim 10, having the following structures:

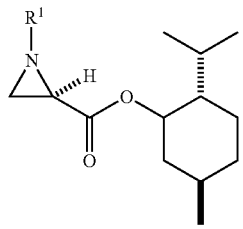

(2R)-[N—R¹]aziridine-2-carboxylate (−)-menthol ester

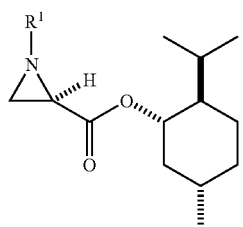

(2R)-[N—R¹]aziridine-2-carboxylate (+)-menthol ester

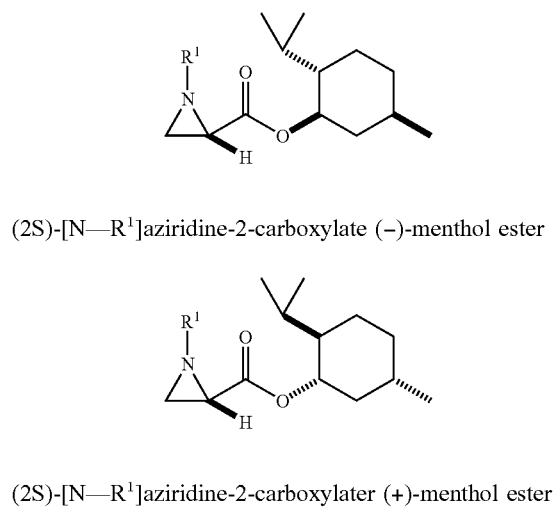

(2S)-[N—R¹]aziridine-2-carboxylate (−)-menthol ester (2S)-[N—R¹]aziridine-2-carboxylater (+)-menthol ester (I)

wherein R¹ is hydrogen; alkyl; cycloalkyl; 4-chlorophenyl; 4-methoxyphenyl; s-triazinyl or pyridinyl acyl; benzyl; hydrocarbon residue which may be substituted with a substituent selected from the group consisting of hydroxy, alkoxy, dialkylamino, phenyl, 4-chlorophenyl, and 4-methoxyphenyl; 2,4-dimethoxyphenyl; substituted phenyl including (1R)-phenylethyl and (1S)-phenylethyl, and menthol is selected from the group consisting of (+)-menthol and (−)-menthol.

16. The compound according to claim 15, wherein the optically active compound of formula I is selected from the group consisting of (2R)-[N-(1R)-phenylethyl]aziridine-2-carboxylate (−)-menthol ester, (2S)-[N-(1R)-phenylethyl]aziridine-2-carboxylate (−)-menthol ester, (2R)-[N-(1S)-phenylethyl]aziridine-2-carboxylate (−)-menthol ester, (2S)-[N-(1S)-phenylethyl]aziridine-2-carboxylate (−)-menthol ester, (2R)-[N-(1R)-phenylethyl]aziridine-2-carboxylate (+)-menthol ester, (2S)-[N-(1R)-phenylethyl]aziridine-2-carboxylate (+)-menthol ester, (2R)-[N-(1S)-phenylethyl]aziridine-2-carboxylate (+)-menthol ester, and (2S)-[N-(1S)-phenylethyl]aziridine-2-carboxylate (+)-menthol ester.

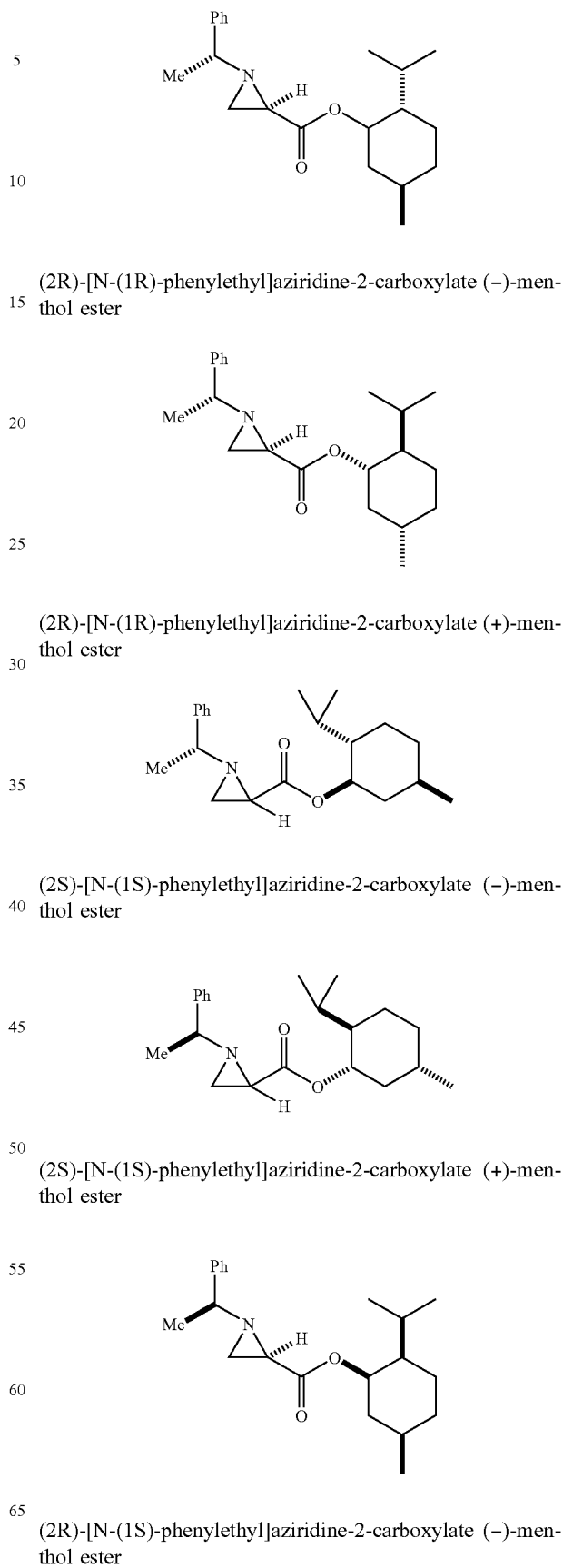

(2R)-[N-(1R)-phenylethyl]aziridine-2-carboxylate (−)-menthol ester (2R)-[N-(1R)-phenylethyl]aziridine-2-carboxylate (+)-menthol ester (2S)-[N-(1S)-phenylethyl]aziridine-2-carboxylate (−)-menthol ester (2S)-[N-(1S)-phenylethyl]aziridine-2-carboxylate (+)-menthol ester (2R)-[N-(1S)-phenylethyl]aziridine-2-carboxylate (−)-menthol ester

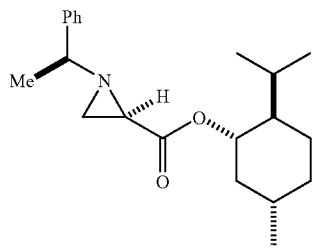

(2R)-[N-(1S)-phenylethyl]aziridine-2-carboxylate (+)-menthol ester

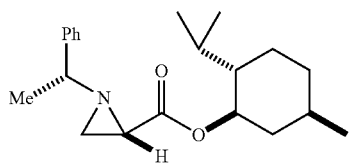

(2S)-[N-(1R)-phenylethyl]aziridine-2-carboxylate (−)-menthol ester (2S)-[N-(1 R)-phenylethyl]aziridine-2-carboxylate (+)-menthol ester.

17. A process for producing optically active aziridine-2-carboxylate derivatives or optically active hydroxymethylaziridine compounds, which comprises transesterification or reduction of the compound as claimed in claim 15.

18. The process according to claim 6, wherein the amine is triethylamine and the inorganic base is potassium carbonate.

19. The process according to claim 13, wherein the alcohol is ethanol and the hydrocarbon solvent is n-hexane.

20. A process for producing optically active aziridine-2-carboxylate derivatives or optically active hydroxymethylaziridine compounds, which comprises transesterification or reduction of the compound as claimed in claim 16.

* * * * *